United States Patent [19]

Lorenz

[11] 4,425,093
[45] Jan. 10, 1984

[54] SPRING ELEMENT FOR ORTHODONTIC PLATES

[76] Inventor: Wilhelm Lorenz, Am Wüllenberg 43, D5277 Marienheide, Fed. Rep. of Germany

[21] Appl. No.: 379,974

[22] Filed: May 19, 1982

[30] Foreign Application Priority Data

May 20, 1981 [DE] Fed. Rep. of Germany ... 8114926[U]
Jul. 30, 1981 [DE] Fed. Rep. of Germany ... 8122384[U]

[51] Int. Cl.$^3$ .............................................. A61C 7/00
[52] U.S. Cl. ................................................... 433/149
[58] Field of Search ..................... 433/6, 7, 18, 21, 149

[56] References Cited

U.S. PATENT DOCUMENTS 2,266,860 12/1941 Griesinger ............................. 433/7
3,837,082 9/1974 Pool ..................................... 433/149
4,273,530 6/1981 Broussard ............................... 433/6

Primary Examiner—Robert Peshock
Attorney, Agent, or Firm—Harold W. Milton, Jr.

[57] ABSTRACT

A novel auxiliary element for orthodontic plates will permit sagittal tooth movements in the region of the side teeth, especially distal movements. The auxiliary element consists of a base of plastic and of a spring element embedded in this base plate and made of an elastic, but permanently deformable material. Depending on the number of teeth to be moved, one or more such spring elements are cast into the base plate and are then activated accordingly, that is to say bent in the appropriate direction. The spring element comprises two clamping arms, one of which is made U-shaped and engages over the adjacent tooth, while the other clamping arm comprises a loop part, one leg of which engages on the tooth to be moved.

5 Claims, 3 Drawing Figures

SPRING ELEMENT FOR ORTHODONTIC PLATES

The invention relates to a spring element for orthodontic plates for achieving sagittal tooth movements in the region of the side teeth, especially distal movements. The known removable treatment devices consist of a base plate and spring elements embedded therein. The said spring elements are used in general for anchoring the said plates, which could be used for hardly more than the transversal extending the jaws. The aforesaid known plates could be used however in a very limited way for distalisation of molar and premolar teeth, since the said plates produced more or less reciprocal forces working in mesial direction in general. Even an additional use of sagittal screws did not give a sufficient result.

The object of the invention is to develop the aforesaid known removable orthodontic plates such way that one or more teeth in the region of the side teeth can be moved thereby in distal direction. This possibility to shift single teeth or even groups of teeth permits to eliminate restricted space in the remaining region of teeth.

It is essential, however, that the said spring elements must not cause a rotation of teeth with respect to their axis and no tilting of the teeth.

The invention resides in the fact that the spring element or each spring element respectively comprises a clamp having two arms and being made of an elastic, but permanently deformable material, which clamp comprises a base part to be embedded into the said plate made of plastic, and a pair of clamping arms projecting from the said base part. The first of said clamping arms is designed as an approximately U-shaped yoke for engaging over the adjacent tooth, whereas the second clamping arm comprises a loop part, one leg of which is provided for engaging over the tooth to be shifted and the other leg of which is provided for engaging over the adjacent tooth. The free ends of the said clamping arms are broadened and are provided for engaging the tooth to be shifted.

The aforesaid broadened free ends of the said clamping arms are preferably sickle-shaped.

The aforesaid clamping element may be made in one piece.

It has been found, however, that a two-piece design of this spring element to be inserted into the base plate offers advantages in comparison with the one-piece design, because these two parts of the spring element can now be brought into the correct position without difficulty on the plaster model of the upper jaw or lower jaw or even more into this position by themselves. In the case of the one-piece spring element, it was still necessary, to achieve the best possible adjustment of the two clamping arms, to carry out bending work which can now be omitted completely or to a large extent.

The base part of this two-piece spring element comprises two separate parts each of which is connected to one or the other of the said clamping arms.

Consequently, the first-mentioned clamping arm of the spring element is embedded in the base plate by one of its free ends, then extends on the inner side of the teeth upwards in the upper jaw or downwards in the lower jaw to the masticatory surface, then bends and runs above the contact point, after which it bends again on the outer side of the particular tooth or of the dental arch and extends in the direction of the tooth root to the gum margin. The free end of this arm is then flattened in the form of a sickle and comes to rest approximately against the tooth to be shifted.

It is to be understood that a pair of mirror-inverted spring elements is required, one of which may be used for the right upper jaw as well as for the left lower jaw, whereas the other one is needed for the left upper jaw or for the right lower jaw, respectively.

The aforesaid clamping arm is made approximately U-shaped when seen from the side, one leg extending within the dental arch and the other extending outside the dental arch and the middle portion of the U extending from the inside outwards above the contact point.

Correspondingly, one end of the other clamping arm is likewise embedded in the base plate and likewise extends within the dental arch in the direction of the masticatory surface, also inclined, as described above, parallel to the first clamping arm and at a distance of about one millimeter. The said clamping arms project from the base plate in the same plane. The angled position of the arms of the spring element after they project from the plate is due to the fact that the spring elements are bent in this form, this being a change which must be mentioned in relation to the form described hitherto. The purpose of this change is that after the spring element has been inserted into the plate, the clamping arms, bent at an angle of 60° in the mesial direction, are both bent up so that they are perpendicular to the plate edge in front of the interdental space of the teeth assigned to them. Since the spring element as a whole has been displaced somewhat from the interdental space as a result of being angled in the mesial direction, the spring element is now in the best possible position. The position of the ends of the spring element, which is changed as a result of this measure, is corrected by twisting these ends distally until there arises in the clamping arms a pre-stress which makes it possible to distalise the teeth without difficulty as a result of torsional elasticity.

The purpose of the measure involving bending the angled clamping arms after completion of the orthodontic plate so that they are arranged perpendicularly in front of the interdental space evolved from tests which revealed a highly relevant effect.

In the case of spring elements which were worked into the plate from the outset with perpendicular clamping arms, in the course of treatment during which the teeth to be moved driftly distally, the flattened ends which initially rested in the best possible way against the tooth, drifted ever further towards the masticatory surface because of the torque of the twisted clamping arms, as a result of which a tilting effect occured increasingly on the tooth. In addition, the end of the clamping arm increasingly took up an angled position to the tooth to be moved and no longer rested flat against the neck of the tooth. Consequently, the effective spring force also decreased, and the progress of treatment was delayed.

The behavior of the spring element according to the invention, in which angled clamping arms are used, is completely different. After the clamping arms projecting from the plate had been bent up perpendicularly and the sickle-shaped anchors had been activated in the necessary way, it was found that the ends of the two arms of the spring element, which were flattened in the form of a sickle, maintained their initial position during the course of treatment. Consequently they did not drift towards the crown and also did not take up an acute-angled position to the tooth, but rested in the best possible way against the neck of the tooth in the vicinity of the gum margin and flat against the tooth wall, so that the spring forces acted on the tooth in the desired way. Model tests confirmed the above-mentioned effect.

Hitherto, it was customary to embed the spring element with clamping arms projecting perpendicularly from the plate, and they were also made to follow the distally drifting teeth by being bent distally. However, the distance of this bend is only half as great as in the above-mentioned method with clamping arms inclined in the mesial direction. As a result, the distalisation of teeth was not possible to the extent described above.

Finally, the second clamping arm extends in the form of a hairpin bend, bridging the first clamping arm, runs back again closely along the masticatory surface, after which it bends again on its inner edge in the direction of the tooth root up to the gum margin and terminates in an end flattened in the form of a sickle. This end comes to rest within the dental arch against the approximal face of the tooth to be shifted. Thus, the two clamping arms act together on the tooth to be shifted, and the latter is prevented from rotating.

Whereas the first-mentioned approximately U-shaped clamping arm, which engages externally on the tooth with its end flattened in the form of a sickle, already has intrinsically a sufficient length, measured from the base plate holding it to the flattened end, and consequently can generate the desired spring effect, a sufficient length of the other clamping arm is obtained by guiding it in the form of the hairpin bend mentioned, from the base plate initially via the masticatory surface of the teeth up to the front edge and then back again.

Thus, the two legs of the loop part of the last-mentioned clamping arm appropriately surround the first clamping arm guided more or less straight beyond the contact point, and come to rest respectively on either side of this first arm, on the masticatory surfaces of the tooth to be shifted, on the one hand, and of the tooth adjacent to this, on the other hand. As a result, a secure retention of the entire plate aid is achieved at the same time, especially if the buccal end of the U-shaped clamping arm is engaging the tooth with its tip in an interdental position.

The two clamping arms forming the spring element are always processed together and in pairs, that is to say they constitute an inseparable unit, but for the reasons mentioned in the introduction are still displaceable relative to one another in the longitudinal direction, that is to say in the transverse direction relative to the dental arch, before being embedded in the base plate.

The invention is explained in more detail below in exemplary embodiments, in which.

Figure 1:
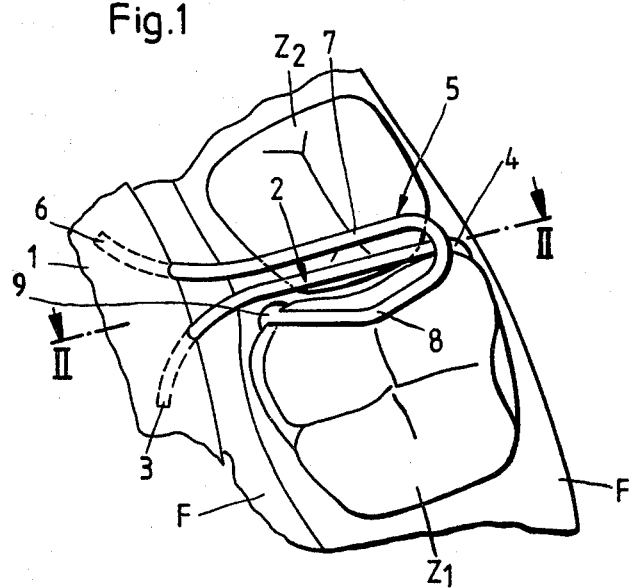
FIG. 1 shows a view of the masticatory surfaces of two adjacent teeth, one of which is to be shifted distally by means of the plate aid.
Figure 2:
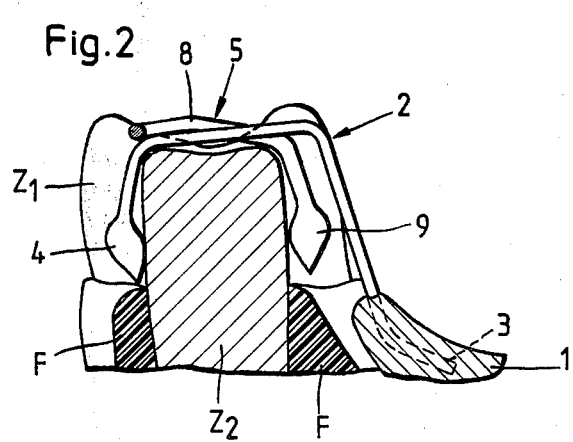
FIG. 2 shows a section along the line II-II in FIG. 1.

The base plate 1, shown only partially in FIG. 1 and FIG. 2, which is inserted within the dental arch consists of plastic and is designed so that it rests by suction against the oral mucosa of the upper jaw or lower jaw.

The plate aid consists of the above-mentioned base plate and of a spring element embedded in this with its base part and consisting of metal wire which is elastic, but permanently deformable.

The spring element projects from the base plate partly distally and partly mesially and rests with its ends, as described in more detail below, against a tooth $Z_1$ to be shifted. FIG. 1 shows this tooth and the tooth $Z_2$ adjacent to it, looking at the masticatory surface in both cases. The section along the line II-II extends in the centre partially through the adjacent tooth $Z_2$. This sectional region is consequently shown in a simplified manner by hatching in FIG. 2. The gum F surrounding the teeth is indicated likewise in FIGS. 1 and 2.

The spring element consists of the two clamping arms 2 and 5, of which the end pieces 3 and 6 located within the dental arch form the base part of the spring element and are embedded in the base plate 1. As may be seen, the end pieces are made to diverge, so as to improve the anchoring in the base plate and reduce the danger of breaking.

The clamping arm 2 extends transversely beyond the point of contact between the two teeth $Z_1$ and $Z_2$ up to the outer side of the tooth $Z_1$ to be shifted and its end 4, widened in the manner of a sickle, comes to rest there approximally against the tooth $Z_1$. The bent end of the clamping arm 2 is twisted a few degrees in the distal direction, so that only the torsional elasticity of the clamping arm exerts its thrust on the tooth.

The other clamping arm 5 comprises a loop part, one leg 7 of which adjoins the embedded end piece 6 and extends along the masticatory surface of the adjacent tooth $Z_2$, whilst the other leg 8, engaging over and, if appropriate, touching the masticatory surface of the tooth $Z_1$ to be shifted, ends in the widened portion 9. Here, too, as in the first clamping arm, only the torsional elasticity of the clamping arm is utilized.

Thus, the tooth $Z_1$ is stressed in the distal direction uniformly and without rotation, and is finally shifted, by means of the two clamping arms via their flattened ends 4 and 9 widened in the form of a sickle.

Figure 3:
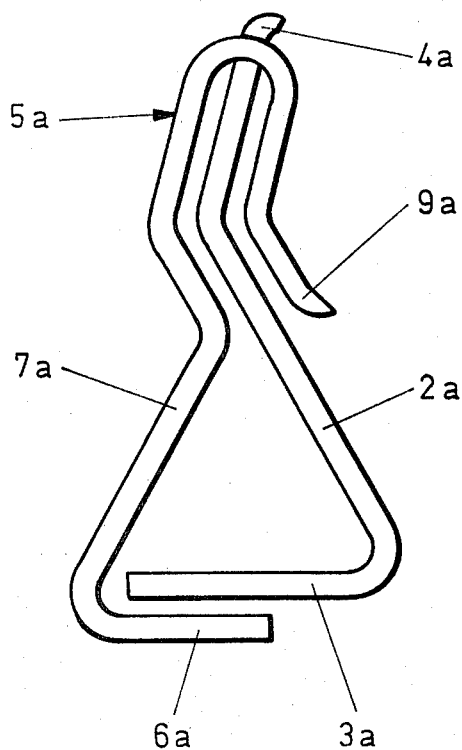
FIG. 3 shows, on an enlarged scale, a representation of a special embodiment of the spring element, before embedding the same in the plate.

FIG. 3 shows an improved design of the spring element consisting of two parts, in which the same reference numerals are used as in FIGS. 1 and 2, but with an additional index "a".

One clamping arm 2a, which is bent slightly at its end engaging over the tooth and (not shown) is provided with a sickle-shaped widened portion, is bent at an acute angle at its other end 3a embedded in the plastic.

The other clamping arm 7a merges at its front end into a hairpin-shaped loop 8a, the free end 9a of which is again widened in the form of a sickle. At its other end this clamping arm is bent again at an acute angle, and, when inserted and subsequently cast in plastic, this end 6a comes to rest approximately parallel to the end 3a of the first-mentioned clamping arm at a short distance from the latter.

What is claimed is:

1. A spring element for orthodontic plates for achieving sagittal tooth movements in the region of the side teeth especially distalisations, characterized in that said spring element comprises clamping means with two arms, said clamping means being made of an elastic, but permanently deformable material and including a base part for embedding the same into the plate made of plastic material, and a pair of clamping arms (2, 5) projecting from said base part (3, 6), the first one (2) of said clamping arms being designed as an approximately U-shaped yoke and engaging over the adjacent tooth ($Z_2$), said U-shaped yoke extending away from said base part (3) and including a first free end (4) while the other one of said arms (5) includes a loop part having one leg (7) extending away from said base part (6) for engaging over an adjacent tooth ($Z_2$) and a second leg (8) extending towards said base part (6) and having a free end 9 being substantially parallel to and spaced from said free end (4) of said first arm (2), said free ends (4, 9) of the said clamping arms (2, 5) being broadened for engaging the tooth ($Z_1$) to be shifted.

2. A spring element according to claim 1, characterized in that the said broadened free ends (4, 9) of the said clamping arms (2, 5) are sickle-shaped.

3. A spring element according to claims 1 or 2, characterized in that the said spring element is a one-piece element.

4. A spring element according to claims 1 or 2, characterized in that the base part of the said spring element consists of two separate parts (3a, 6a), each of which being connected with one or the other of the said clamping arms (2a, 5a), respectively.

5. A spring element according to claim 1 or 2, characterized in that the two clamping arms are bent at an angle of 60° in mesial direction after projecting from the material of the plate and are then bent so that, being perpendicular to the plate edge in front of the interdental gap, they are activated by twisting the clamping arms.

* * * * *